United States Patent [19]

Schafer et al.

[11] 4,104,304

[45] Aug. 1, 1978

[54] PRODUCTION OF METHYLDICHLOROPHOSPHANE

[75] Inventors: Stefan Schäfer, Brühl; Klaus Gehrmann; Alexander Ohorodnik, both of Erftstadt; Karl-Heinz Steil, Hürth; Wernfried Riechmann, Brühl; Friedhelm Bylsma, Erftstadt, all of Fed. Rep. of Germany

[73] Assignee: Hoechst Aktiengesellschaft, Frankfurt am Main, Fed. Rep. of Germany

[21] Appl. No.: 814,465

[22] Filed: Jul. 11, 1977

[30] Foreign Application Priority Data

Jul. 14, 1976 [DE] Fed. Rep. of Germany ....... 2631608
Apr. 26, 1977 [DE] Fed. Rep. of Germany ....... 2718391

[51] Int. Cl.$^2$ ............................. C07F 9/52; C07F 9/02
[52] U.S. Cl. .................................................. 260/543 P
[58] Field of Search ..................................... 260/543 P

[56] References Cited

U.S. PATENT DOCUMENTS 3,210,418  10/1965  Pianfetti ........................... 260/543 P

FOREIGN PATENT DOCUMENTS 2,046,314  5/1976  Fed. Rep. of Germany.
2,629,299  12/1977  Fed. Rep. of Germany.
7,013,363  3/1972  Netherlands.

OTHER PUBLICATIONS

Pianfetti et al., J. Am. Chem. Soc., vol. 84, pp. 851–854 (1962).

*Primary Examiner*—Gerald A. Schwartz
*Attorney, Agent, or Firm*—Connolly & Hutz

[57] ABSTRACT

Production of methyldichlorophosphane. The compound is made by reacting methane and phosphorus trichloride in a reaction zone in which a temperature higher than 500° C is maintained. More specifically, hot reaction gas coming from the reaction zone is mechanically freed from solid matter, and the reaction gas freed from solid matter is passed to a quenching zone in which it is quenched with liquefied reaction mixture having 0.3 to 5 weight % of an organic barium compound or a non-ionic surfactant dissolved therein.

6 Claims, 1 Drawing Figure

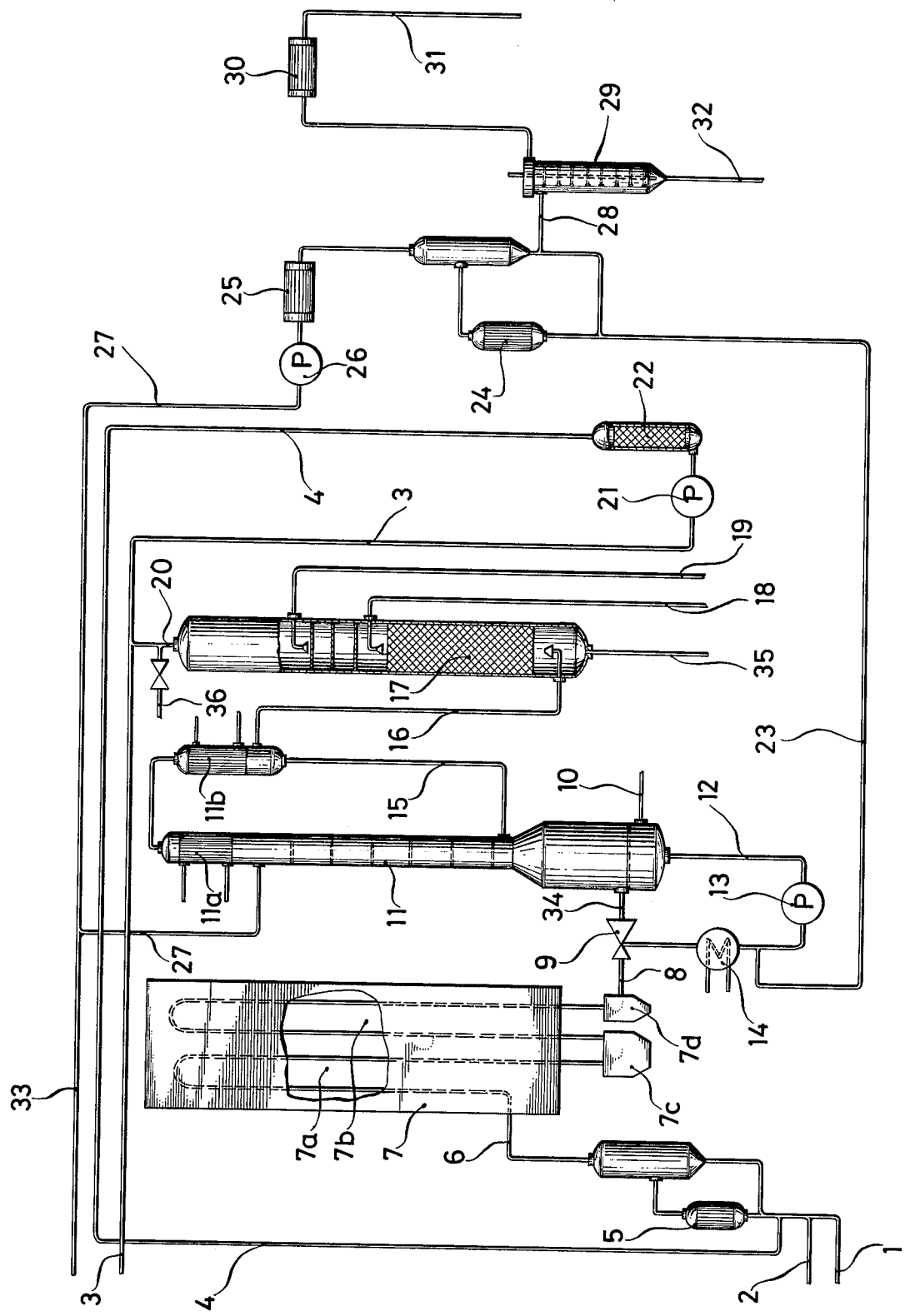

PRODUCTION OF METHYLDICHLOROPHOSPHANE

This invention relates to the production of methyldichlorophosphane. A process for making this compound has been described in German patent applications Nos. P 2629, 299.9 and P 2701, 389.4, wherein methane and phosphorus trichloride are reacted in contact with carbon tetrachloride at temperatures higher than 500° C; more specifically, the starting mixture employed in this prior process is admixed with 2 to 7 mol % of reaction-initiating carbon tetrachloride, based on the phosphorus trichloride, the carbon tetrachloride is made to react to an extent of 50 to 80% by adjusting the reaction temperature within the range 550° to 650° C for constant residence times of 0.1 to 0.9 second, and the resulting reaction mixture, containing a residual analytically observable 20 to 50% proportion of the carbon tetrachloride used, is condensed.

Methyldichlorophosphane ($H_3C-PCl_2$) is a compound which is of interest not only in preparative chemistry but also, and to an increasing extent, as a starting material for making flameproof fibers and synthetic resins.

Special problems which are encountered in the production of methyldichlorophosphane are the following. The starting material ($PCl_3$; $bp_{760} = 74.5°$ C) has a boiling point which is only slightly different from that of the product ($CH_3-PCl_2$; $bp_{760} = 81°$ C). In addition, methyldichlorophosphane tends to be decomposed catalytically by various substances. In the processes described heretofore, methyldichlorophosphane is made from $PCl_3$ and $CH_4$ in a single passage reaction, i.e., without any immediate recycling of unreacted starting material. As described in the literature, this operation is relatively easy to carry out, but precipitating solid matter may cause serious complications in practice.

As the maximum allowable concentration in the production locality (the "MAC") of the material concerned is less than 1 ppm, it is clearly necessary that the process for making the methyldichlorophosphane should be assessed not only in its commercial aspects but also in its aspects relating to environmental conservation and the health of the operating personnel, cleaning operations being entailed which involve a highly potentially injurious material.

Inasmuch as neither the $CH_4$ nor the $PCl_3$ is fully converted into $H_3C-PCl_2$ in the reaction of $CH_4$ with $PCl_3$, it is furthermore mandatory that unreacted starting materials (which may be more than 80% of the quantity used) should be recycled if the plant is to be operated under commercially attractive conditions.

Practical experience has however shown that the complications caused by precipitating solid matter can be even more serious when unreacted starting materials are recycled than in a single passage reaction. By reducing the conversion rate, it is possible in principle to counteract the tendency of the solid material to precipitate. This measure has however serious adverse effects on the economy of the process, and does not permit the problem of the separation of solid matter to be resolved satisfactorily in practice because of the special properties of the particular substances concerned. More specifically a serious problem arises here because of the tendency of methyldichlorophosphane to undergo decomposition into $PCl_3$ and salt-like solid matter, in contact with various materials.

At temperature near the above-mentioned boiling points, i.e., at temperatures somewhat above 70° C, pure methyldichlorophosphane and freshly distilled mixtures of methyldichlorophosphane and phosphorus trichloride are liable to undergo the following reactions:

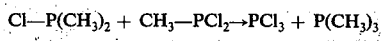

These entail the formation of salt-like solid material of uncertain constitution, and it is not possible, by means only or ordinary techniques like distillation, to keep the apparatus free from deposits and to ensure that it will remain operational.

Inasmuch as $PCl_3$, as also methyldichlorophosphane, can scarcely be expected to dissolve the salt-like compounds in question, these latter are very liable to deposit predominantly on the surfaces of heat exchangers. Solid matter which deposits thereon can so impair the functioning of the respective apparatus components that they have to be cleaned after very short periods of operation.

It has however been found that $PCl_3$, as also methyldichlorophosphane, is neither corrosive nor self-ignitible in a closed system, i.e., with the exclusion of air and moisture. All of the disadvantageous effects described hereinabove, including those which may be injurious to health, arise exclusively from the opening of the apparatus for cleaning purposes. No fully satisfactory means for recycling unreacted starting materials have heretofore been described in connection with processes having $PH_3$- conversion rates of 10 to 30%, the $CH_4$-conversion rates associated therewith being, it may be added, even lower.

It is an object of the present invention to provide a process which is free from the disadvantages described hereinabove, wherein measures for reducing the formation of the various by-products are employed in combination with measures for inhibiting the precipitation of solid matter and for preventing the apparatus used from being rendered inoperative.

The present invention provides more specifically a process for making methyldichlorophosphane by reacting methane and phosphorus trichloride in a reaction zone in which a temperature higher than 500° C is maintained, in which process hot reaction gas coming from the reaction zone is freed from solid matter, and the reaction gas freed from solid matter is passed to a quenching zone in which it is quenced with liquified reaction mixture having 0.3 to 5 weight %, preferably 0.5 to 3 weight %, of an organic barium compound or a non-ionic surfactant dissolved therein.

Preferred features of the present process comprise:
(a) heating the reaction zone electrically from the outside, the reaction zone comprising a preliminary heating zone and a principal heating zone, the outlet of the preliminary heating zone being connected by means of a solid matter separating zone to the inlet of the principal heating zone, the outlet of the principal heating zone being connected by means of another solid matter separating zone to the inlet of a quenching zone, and each of the two solid matter separating zones being disposed outside the electrically heated reaction zone;
(b) operating the quenching zone on the principle of a Venturi tube;

(c) separating the quenched hot reaction gas into a gas phase and liquid reaction mixture, the latter being admixed with the soluble organic barium compound or soluble non-ionic surfactant and being recycled as quenching liquid via a cooling zone to the quenching zone;

(d) freeing unreacted methane and hydrogen chloride in the gas phase from vapor-phase phosphorus trichloride and methyldichlorophosphane by condensation effected by cooling in two stages down to −40° to −55° C; the resulting condensate being recycled by being incorporated in the liquid reaction mixture employed as the quenching liquid; the uncondensed portion of the gas phase being delivered to a scrubbing zone and freed therein from hydrogen chloride by initially spraying water and subsequently spraying sodium hydroxide solution thereonto; and the resulting purified gaseous methane being compressed, dried and recycled to the reaction zone;

(e) withdrawing continuously a portion of the liquid reaction mixture employed as the quenching liquid; subjecting said portion to distillation so as to distil off some of the phosphorus trichloride and some of the methyldichlorophosphane therefrom and recycling the material so distilled off to serve as quenching liquid, in admixture with the soluble organic barium compound or soluble non-ionic surfactant; removing the distillation sump product comprising liquefied reaction mixture at a rate sufficient to remove the methyldichlorophosphane as fast as it is being continuously formed; delivering said sump product to a thin film evaporator and distilling off from non-volatile contaminants the phosphorus trichloride and methyldichlorophosphane present therein; and recovering pure methyldichlorophosphane from the resulting distillate containing phosphorus trichloride and methyldichlorophosphane;

(f) using a soluble barium phenate-sulfonate mixture as the organic barium compound;

(g) using an ethoxylated unbranched fatty alcohol having 6 to 30 carbon atoms as the non-ionic surfactant; and (h) using a polymeric surfactant derived from ethylene oxide or from ethylene oxide and propylene oxide as the non-ionic surfactant.

The present process for making methyldichlorophosphane is preferably carried out, as described in German patent applications Nos. P 2,629,299.9 and P 2,701,389.4, by reacting methane with phosphorus trichloride in contact with 2 to 7 mol %, based on the phosphorus trichloride, of reaction-initiating carbon tetrachloride, the carbon tetrachloride being made to react to an extent of 50 to 80% by adjusting the reaction temperature within the range 500° to 650° C for constant residence times of 0.1 to 0.9 second.

A procedure falling within the scope of the present invention will now be described by way of example with reference to the accompanying drawing, the single FIGURE of which is a diagrammatic side view of an apparatus employed in the said procedure.

In the apparatus shown in the FIGURE, $PCl_3$ coming from a conduit 1 and $CCl_4$ coming from a conduit 2 are supplied in a ratio such that the resulting liquid mixture contains 2 to 7 mol % of $CCl_4$. Methane is introduced into the apparatus through a conduit 3, and is conveyed together with the $PCl_3$—$CCl_4$ mixture through a conduit 4 to a circulation evaporator 5 in which the methane is saturated with the $PCl_3$—$CCl_4$ mixture at a predetermined elevated temperature. In this manner, it is ensured that a gas mixture with a predetermined constant molar ratio of $CH_4:PCl_3:CCl_4$ is continuously introduced through a conduit 6 into an electrically heated tubular reactor 7. The latter is subdivided into a preliminary heating zone 7a and a principal heating zone 7b. In the preliminary heating zone 7a, the gas mixture is heated to a reaction temperature in the range 501°–650° C, and in the principal heating zone 7b it is maintained at a constant reaction temperature. A tubular reactor so subdivided into two zones has proved advantageous with respect to the maintenance of predetermined residence times. The arrangement of the two zones of the reactor 7 is such that the outlet of the preliminary heating zone 7a is connected to the inlet of the principal heating zone 7b by way of a first solid matter separating zone 7c, which is disposed outside the actual heated region of the reactor 7. The outlet of the principal heating zone 7b is connected, again outside the heated region, to a second solid matter separating zone 7d. By this arrangement, solid matter is effectively prevented from penetrating into the liquid circulation system downstream of the reactor 7.

From the second solid matter separating zone 7d, the hot gaseous reaction mixture is delivered via a conduit 8 to a quenching system 9 operating on the principle of a Venturi tube. The quenching system 9 employs a quenching liquid constituted by the reaction mixture, which is continuously liquefied in the present procedure and which is admixed, by means of a conduit 33, with 0.3 to 5 weight % of an organic barium compound or non-ionic surfactant soluble therein. By means of a conduit 12 and a pump 13, this liquefied reaction mixture is taken from the sump of a quenching column 11, and a portion of it is precooled in a heat exchanger 14, and fed back to the quenching system 9, in which the hot gaseous reaction mixture entering via the conduit 8 is quenched, separating into a gas phase and a liquid phase (liquefied reaction mixture). Both of these two phases are delivered through a conduit 34 to the quenching column 11. The gas phase consists substantially of unreacted methane, hydrogen chloride, formed in accordance with the following reaction equation:

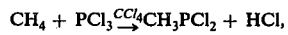

$$CH_4 + PCl_3 \overset{CCl_4}{\rightarrow} CH_3PCl_2 + HCl,$$

and vapor-phase fractions of the $PCl_3$ and $CH_3PCl_2$. Inasmuch as HCl retards the reaction, it is necessary that the methane, which is to be recycled, should first be freed therefrom.

In order to keep the loss of material which is associated with this operation as low as possible, it is good practice to free the gas phase first from the above-mentioned vapor-phase fractions of the $PCl_3$ and $CH_3PCl_2$. This is done using the quenching column 11 by cooling the gas phase initially in a cooler 11a wherein it is cooled down to −10° to +10° C, and then in a cooler 11b wherein it is cooled down to −40 to −55° C. The condensate so obtained is recycled to the quenching column 11 through a conduit 15.

A conduit 10 is provided through which $PCl_3$ by itself can be introduced into the quenching column 11 to provide quenching liquid at the start of continuous operation, i.e., for the purpose of priming only.

The gas phase which has largely been freed from phosphorus compounds is introduced, on leaving the cooler 11*b*, through a conduit 16, into the bottom portion of a scrubbing column 17. This gas phase, which contains HCl, passes through a lower portion of the column 17, which is packed with filling material and which is countercurrently supplied from above with water coming from a conduit 18; this enables the gas phase to be freed from the bulk of the hydrogen chloride. The remaining methane is further purified in the middle portion of the column 17, which is provided with bubble trays and which is supplied from above with dilute sodium hydroxide solution, through a conduit 19. The combined NaCl and HCl containing waste waters are taken from the bottom of the scrubbing column 17 through a conduit 35.

Purified methane is taken from the scrubbing column 17 through a conduit 20 and combined with fresh methane supplied through the conduit 3. The combined methane is compressed by means of a pump 21, and passed to a drier 22. The latter contains a drying agent, e.g., silica gel, serving to free the methane from water down to a residual content of at most 25 ppm, preferably 10 ppm. The dried methane is conveyed through the conduit 4 to the circulation evaporator 5. A mixture of air and nitrogen or methane and nitrogen may be drawn in through a conduit 36 at the start of continuous operation.

A portion of the liquefied reaction mixture taken from the quenching column 11 is withdrawn on the high-pressure side of the pump 13, but upstream of the heat exchanger 14, and conveyed through a conduit 23 to a further circulation evaporator 24. This latter is so operated as to ensure that some of the freshly produced methyldichlorophosphane, some of the unreacted $PCl_3$ and whatever by-products are formed remain in its base, while a mixture comprising the remainder of the methyldichlorophosphane and the remainder of the $PCl_3$ is distilled off overhead; this mixture is condensed in a condenser 25 and recycled by means of a pump 26 and through a conduit 27 to the quenching column 11. This permits the partial removal of undesirable by-products which would be liable to adversely affect the quenching liquid cycle, i.e., the system comprising components 9, 11, 12, 13 and 14.

The liquid accumulating in the base of the circulation evaporator 24 is introduced through a conduit 28 into a thin-film evaporator 29, in which it is separated into a distillate consisting of a mixture of $PCl_3$ and methyldichlorophosphane and a residue, which is continuously removed through a conduit 32 and discarded. The distillate is liquefied in a cooler 30 and removed through a conduit 31. It contains 15 to 25 weight % of methyldichlorophosphane and 1-2 weight % of $CCl_4$, the balance being $PCl_3$. This purified preliminary product can be converted into the desired pure methyldichlorophosphane by ordinary distillation, or by the process described in U.S. Pat. No. 3,519,685.

The present process enables methyldichlorophosphane to be reliably produced, over long operational periods, with $PCl_3$-conversion rates of 20 to 26%. In the absence of the organic barium compound or non-ionic surfactant, which is introduced through the conduit 33, successful operation is limited to several days for $PCl_3$-conversion rates of 10 to 15%, or even limited to hours for a 20% conversion rate of $PCl_3$.

The following Examples illustrate the invention, and relate to procedures employing an apparatus as described above with reference to the accompanying drawing.

EXAMPLE 1

Nitrogen was admitted through the conduit 3 to replace the air initially present, and the nitrogen was then replaced by methane. To this end, a suitable quantity of gas was taken from the gas under circulation, through the conduit 36. Next, the base of the quenching column 11 and the quenching cycle units 12, 13, 14, 9 were filled, through the conduit 10, with $PCl_3$, and the pump 13 and the heat exchanger 14 were set in operation. In the meantime, the preliminary heating zone 7*a* was gradually heated electrically to 550° C, and the principal heating zone 7*b* was similarly heated to 565° C, whereas a temperature of −5° C was established in the cooler 11*a* and a temperature of −50° C was established in the cooler 11*b*.

Next, 100 kg/h of $PCl_3$ (through the conduit 1), 4 kg/h of $CCl_4$ (through the conduit 2) and 90 normal m³/h (S.T.P.) of methane (through the conduit 4) were introduced into the circulation evaporator 5 at a constant liquid temperature of 40° C. This corresponded, under the pressure conditions prevailing in the apparatus, to a molar ratio of $PCl_3$ to methane of 1:4.3, in the reactor. The residence time of the starting mixture in the principal heating zone 7*b* of the tubular reactor 7 was 0.4 second.

Methane which was consumed during the reaction (3.3 normal m³/h) was continuously replaced by fresh methane admitted through the conduit 3. In order to minimize the escape of vapour-phase $PCl_3$ and $CH_3PCl_2$, the gas phase in the quenching column 11 was cooled down to −50° C. The unreacted methane was freed from HCl by washing with NaOH and water in the scrubbing column 17. Unreacted methane was recovered and compressed by the pump 21 and partially freed in this step from moisture. Prior to the recycling of the methane so purified to the circulation evaporator 5, it was delivered to the drier 22 which was filled with silica gel and dried therein so as to contain less than 10 ppm of water. The quenching liquid cycle was set in operation and the liquid phase was admixed at the same time with 1.5 kg/h of a soluble barium phenate-sulfonate mixture ("ADDITIN RC 1387", a commercially available product of Rhein-Chemie, Rheinau GmbH, Mannheim; ADDITIN is a registered Trade Mark of Bayer AG., Leverkusen). This measure permitted the deposition of solid by-products, especially on the surfaces of the heat exchanger 14 and circulation evaporator 24, to be avoided. A portion of by-products which would adversely affect operation was removed from the quenching liquid cycle by removing a portion of the liquefied reaction mixture through the conduit 23 and introducing it into the circulation evaporator 24. All non-volatile by-products which would be liable to adversely affect operation were retained in the base portion of the circulation evaporator 24, whereas a mixture of methyldichlorophosphane and $PCl_3$ free from solid matter was distilled off overhead, collected in the cooler 25 and recycled by means of the pump 26 and through the conduit 27 to the quenching liquid cycle.

After all the units of the apparatus were found to be working as desired, reaction mixture was continuously taken from the circulation evaporator 24 through the conduit 28 at a rate sufficient to remove the methyldichlorophosphane as fast as it was formed. Under the reaction conditions described, 20.2 mol % of $PCl_3$ underwent conversion to methyldichlorophosphane.

101.7 kg/h of reaction mixture was removed through the conduit 28. This was composed of:
16.8 weight % of methyldichlorophosphane,
2.0 weight % of carbon tetrachloride,
1.1 weight % of chloroform,
0.2 weight % of phosphorus oxychloride,
1.4 weight % of non-volatile fractions of "ADDITIN RC 1387," and
0.2 weight % of unidentified constituents, the balance being phosphorus trichloride.

1.5 kg/h of non-volatile contaminants was removed as base product from the thin film evaporator 29 through the conduit 32. Downstream of the cooler 30 there was obtained 100.2 kg/h of crude product containing 17 weight % of methyldichlorophosphane.

The apparatus described permitted methyldichlorophosphane to be reliably produced under the conditions described for substantially unlimited periods of time. The crude product obtained was treated in known manner so as to isolate the methyldichlorophosphane therefrom.

EXAMPLE 2

The apparatus and reaction conditions were as described in Example 1, but the quantity of carbon tetrachloride which was admitted through the conduit 2 was increased from 4 to 5 kg/h. Also, by supplying more heat, the temperature in the reactor 7 was increased gradually to 580° C, whereby the rate of conversion of the $PCl_3$ to methyldichlorophosphane was increased from 20.2 to 26 mol %. Associated with this increased conversion rate was an increased tendency of solid matter to deposit on the heat exchangers, and low heat transmission coefficients gave evidence of the extent of such deposition. In other words, to achieve the same cooling effect, the coolant had to be used at a lower temperature for cooling a surface affected by this deposition than for cooling a clean surface, or higher temperatures had to be used for evaporation.

The heat exchanger surfaces were however found to remain clean, and the apparatus worked reliably over long periods of time when the proportion of ADDITIN RC 1387 was increased from 1.5 to 2.0 l/h for the above-mentioned increased conversion rate.

EXAMPLE 3

Example 1 was repeated but the preliminary heating zone 7a was heated to 501° C and the principal heating zone 7b was heated to 535° C. The quenching liquid cycle was set in operation and the liquid phase was admixed, through the conduit 33, with 1.5 kg/h of an ethoxylated unbranched $C_{16}$–$C_{18}$ fatty alcohol (molar ratio: 7 $OC_2H_5$-groups: 1 OH-group), which was substituted for ADDITIN RC 1387. The results obtained were as in Example 1, save that 101.7 kg/h of reaction mixture was taken from the conduit 28, and the reaction mixture had a composition slightly different from that indicated in Example 1; more specifically it was composed of:
16.9 weight % of methyldichlorophosphane,
2.1 weight % of carbon tetrachloride,
1.0 weight % of chloroform,
0.2 weight % of phosphorus oxychloride,
1.5 weight % of non-volatile fractions originating from the ethoxylated $C_{16}$–$C_{18}$ fatty alcohol, and
0.2 weight % of unidentified constituents, the balance being phosphorus trichloride.

EXAMPLE 4

The apparatus and conditions were as described in Example 3, but 1.5 kg of a more highly ethoxylated unbranched $C_{16}$–$C_{18}$ fatty alcohol (molar ratio: 80 $OC_2H_5$-groups: 1 OH-group) was used to prevent the deposition of solid by-products.

The rate of conversion of the $PCl_3$ to methyldichlorophosphane was 24 mol %, and the apparatus worked reliably over long periods of time.

EXAMPLE 5

1.4 kg of an ethylene oxide polymer (molecular weight = 4000) was used to prevent the deposition of solid by-products under the conditions described in Example 3.

The rate of conversion of the $PCl_3$ to methyldichlorophosphane was 21 mol %, and the apparatus worked reliably over long periods of time.

EXAMPLE 6

1.4 kg of an ethylene oxide/propylene oxide copolymer (molar ratio = 38:62) was used to prevent the deposition of solid matter under the conditions described in Example 3.

The rate of conversion of the $PCl_3$ to methyldichlorophosphane was 26 mol %, and the apparatus worked reliably over long periods of time.

EXAMPLE 7

Methyldichlorophosphane was made continuously in the apparatus and under the conditions described in Example 1, except that no ADDITIN RC 1387 or non-ionic surfactant was supplied through the conduit 33. After only 2 hours of operation without either of these additives, solid matter was found to have deposited on the heat exchanger 14 and circulation evaporator 24 so that they functioned at only about 85% of their normal efficiency. After 10 hours of operation in the absence of ADDITIN RC 1387 or non-ionic surfactant, it was necessary to discontinue operation.

We claim:
1. A process for making methyldichlorophosphane by reacting methane and phosphorus trichloride in a reaction zone in which a temperature higher than 500° C is maintained, which comprises mechanically freeing hot reaction gas coming from the reaction zone from solid matter, and passing the reaction gas freed from solid matter to a quenching zone in which it is quenched with liquefied reaction mixture having 0.3 to 5 weight % of a soluble barium phenate-sulfonate mixture or a non-ionic surfactant dissolved therein wherein an ethoxylated unbranched fatty alcohol having 6 to 30 carbon atoms or wherein a polymeric surfactant derived from ethylene oxide or from ethylene oxide and propylene oxide is used as the non-ionic surfactant.

2. A process as claimed in claim 1, wherein the reaction zone is heated electrically from the outside and comprises a preliminary heating zone and a principal heating zone, the outlet of the preliminary heating zone being connected by means of a solid matter separating zone to the inlet of the principal heating zone, the outlet of the principal heating zone being connected by means of another solid matter separating zone to the inlet of the quenching zone, and each of the two solid matter separating zones being disposed outside the electrically heated reaction zone.

3. A process as claimed in claim 1, wherein the hot reaction gas freed from solid matter is quenched in a quenching zone operated on the principle of a Venturi tube.

4. A process as claimed in claim 1, wherein the hot reaction gas quenched and separated into a gas phase and liquid reaction mixture, the latter being admixed with the soluble organic barium compound or soluble non-ionic surfactant and being recycled as quenching liquid via a cooling zone to the quenching zone.

5. A process as claimed in claim 4, wherein unreacted methane and hydrogen chloride in the gas phase are freed from vapor-phase phosphorus trichloride and methyldichlorophosphane by condensation effected by cooling in two stages down to $-55°$ C; the resulting condensate being recycled by being incorporated in the liquid reaction mixture employed as the quenching liquid; the uncondensed portion of the gas phase being delivered to a scrubbing zone and freed therein from hydrogen chloride by initially spraying water and subsequently spraying sodium hydroxide solution thereonto; and the resulting purified gaseous methane being compressed, dried and recycled to the reaction zone.

6. A process as claimed in claim 4, which comprises withdrawing continuously a portion of the liquid reaction mixture employed as the quenching liquid; subjecting said portion to distillation so as to distil off some of the phosphorus trichloride and some of the methyldichlorophosphane therefrom and recycling the material so distilled off to serve as quenching liquid, in admixture with the soluble organic barium compound or soluble non-ionic surfactant; removing the distillation sump product comprising liquefied reaction mixture at a rate sufficient to remove the methyldichlorophosphane as fast as it is being continuously formed; delivering said sump product to a thin film evaporator and distilling off from non-volatile contaminants the phosphorus trichloride and methyldichlorophosphane present therein; and recovering pure methyldichlorophosphane from the resulting distillate containing phosphorus trichloride and methyldichlorophosphane.

* * * * *